United States Patent [19]

Reiner

[11] Patent Number: 4,865,765

[45] Date of Patent: Sep. 12, 1989

[54] URSODEOXYCHOLIC ACID DERIVATIVES AND THEIR INORGANIC AND ORGANIC SALTS HAVING THERAPEUTIC ACTIVITY, AND PROCESS FOR PREPARING THE SAME

[75] Inventor: Alberto Reiner, Como, Italy

[73] Assignee: Jago Research AG, Hergiswill, Switzerland

[21] Appl. No.: 121,257

[22] Filed: Nov. 16, 1987

[30] Foreign Application Priority Data

Nov. 26, 1986 [CH] Switzerland ................ 04729/86

[51] Int. Cl.$^4$ .................................... C07J 1/00
[52] U.S. Cl. ................................... 260/397.1
[58] Field of Search ..................... 260/397.1

[56] References Cited

PUBLICATIONS

Chemical Abstracts, vol. 89 (1978) #99630c; Ota et al.

Primary Examiner—Douglas W. Robinson
Assistant Examiner—Joseph A. Lipovsky

Attorney, Agent, or Firm—Armstrong, Nikaido Marmelstein Kubovcik & Murray

[57] ABSTRACT

Ursodeoxycholic acid amides of the formula:

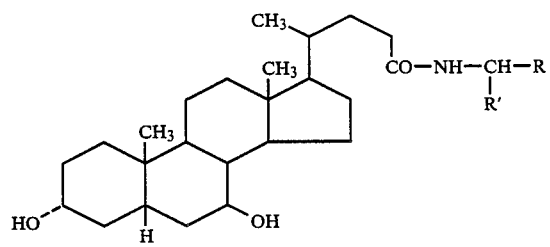

wherein R is —$CH_2$—$SO_3H$ or —COOH and R' is —H and —$(CH_2)_2$—CONH, —$CH_2$—$CONH_2$, —$(CH_2)_2$—$SCH_3$ or —$CH_2$—S—$CH_2$—$CH_2$—COOH, and their salts with inorganic and organic pharmaceutically active bases, are useful in the treatment of altered biligenetic functions and lithiasis or dyskinesia of the biliary ducts.

11 Claims, No Drawings

URSODEOXYCHOLIC ACID DERIVATIVES AND THEIR INORGANIC AND ORGANIC SALTS HAVING THERAPEUTIC ACTIVITY, AND PROCESS FOR PREPARING THE SAME

The present invention relates to amides of ursodeoxycholic acid and to a process for preparing those amides.

The amides of the present invention have the formula:

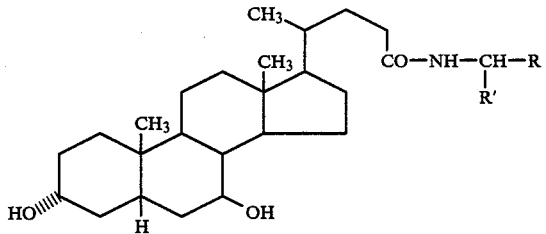

wherein:

$R = -CH_2-SO_3H$ and $R' = -H$ or:

$R = -COOH$ and $R' = CH_2-CH_2-CONH_2$; $-CH_2-CONH_2$; $-CH_2-CH_2-SCH_3$; or $-CH_2-S-CH_2-COOH$, as well as their organic salts with pharmaceutically active bases. These amides are useful in the treatment of altered biligenetic functions, lithiasis or diskinesya of the biliary ducts.

The present invention also includes the salts of those amides with aminoacids, such as lysine or arginine, or with inorganic ions such as Na, Ca, etc.

The present invention also includes a process for preparing those amides and pharmaceutical compositions containing them.

The preparative process involves two steps:

(1) the preparation of a mixed anhydride of ursodeoxycholic acid with ethyl, phenyl or isobutyl chloroformate;

(2) the reaction of the mixed anhydride with appropriate, reactive compounds, containing an $-NH_2$ group, to form the amide bond.

In step (1), the mixed anhydride of ursodeoxycholic acid is prepared at a temperature in the range between 6° and 20° C., using dioxane as solvent, from isobutyl, phenyl or ethyl chloroformate, in the presence of two moles of triethylamine. Formation of the mixed anhydride takes about one hour with constant stirring.

In step (2), the mixed anhydride is reacted with the $-NH_2$ group containing reagent, at a low temperature and in the presence of an organic amine. After the reaction is completed, the following derivatives are obtained:

| | | |
|---|---|---|
| (a) when | $R = -CH_2-CH_2-SO_3H$ | |
| | $R' = -H$ | TAURINAMIDE |
| (b) when | $R = -COOH$ | |
| | $R' = -(CH_2)_2-CONH_2$ | GLUTAMINAMIDE |
| (c) when | $R = -COOH$ | |
| | $R' = -CH_2-CONH_2$ | ASPARAGINAMIDE |
| (d) when | $R = -COOH$ | |
| | $R' = -CH_2-CH_2-S-CH_3$ | METHIONINAMIDE |
| (e) and when | | |
| | $R = -COOH$ | |
| | $R' = -CH_2-S-CH_2-COOH$ | CARBOXYMETHYL-CYSTEINAMIDE. |

The process according to the present invention will be now explained with reference to the following examples.

EXAMPLE 1

Methioninamide of ursodeoxycholic acid, ($R = -COOH$; $R' = -CH_2-CH_2-S-CH_3$).

(a) Preparation of mixed anhydride

To a suspension of 66.7 g of ursodeoxycholic acid in dioxane, 13.3 ml of ethyl chloroformate are added, and the temperature of the reaction mixture is adjusted to between 0° and 10° C. A dioxane solution of an organic amine, preferably triethylamine, is slowly added, and the heterogeneous, white material formed is then heated to room temperature.

(b) Formation of amide

An aqueous solution of 27.9 g of a methionine salt with an organic amine is slowly added to the mixture resulting from (a) and cooled to a low temperature. The heterogeneous, white material becomes progressively more fluid, giving rise to a colorless solution when the addition is completed.

The temperature of the solution is allowed to increase spontaneously to 27°-29° C. over a period of about 5 hours, and carbon dioxide is evolved. When the preparation of the amide is completed, it is separated by dilution of the reaction mixture with aqueous HCl and successive extracted with an organic solvent. The organic phase is washed, with stirring, with an aqueous solution of $NaHCO_3$, the two phases are separated and the aqueous phase acidified with vigorous stirring. White crystals precipitate over a period of about 4 hours, and the crystalline product, filtered under vacuum, is chromatographically pure.

Analysis by quantitative, alkalimetric analysis is 98.51%, the amount of free ursodeoxycholic acid being less than 0.3%. The melting point determination in a capillary tube shows some decomposition at 90° C., but the substance is perfectly clear a 107° C. NMR and R spectra confirm the structural formula and are shown in FIGS. 1 and 2, respectively. No absorption is observed in the UV region for this compound and the compounds of the other Examples.

EXAMPLE 2

Carboxymethyl-Cysteinamide of ursodeoxycholic acid ($R = -COOH$; $R' = -CH_2-S-CH_2-COOH$)

The preparation follows Example 1 very closely employing a sufficient amount of amine to neutralize both of the carboxy groups in carboxymethylcysteine. Using the procedure employed in Example 1, the product is obtained in the form of a microcrystalline, white powder, chromatographically pure, melting at 55° C. The amount of free ursodeoxycholic acid by quantitative alkalimetric analysis, is less than 0.5%, and the NMR and R spectra, shown in FIGS. 3 and 4, confirm the structural formula.

EXAMPLE 3

Asparaginamide of ursodeoxychlic acid. (R=—COOH; R'=—CH₂CONH₂).

After preparation of the mixed anhydride, the formation of the amide occurs at a low temperature by slowly adding the triethylamine salt, and the reaction is completed in about 6–8 hours. Following the procedure of Example 1, a white crystalline product is obtained, which is chromatographically pure. It melts at 117° C., with decomposition at 90° C. The assay by quantitative, alkalimetric analysis is 99%, and the amount of free ursodeoxycholic acid is less than 0.5%. The NMR and R spectra shown in FIGS. 5 and 6 confirm the structural formula.

EXAMPLE 4

Glutaminamide of ursodeoxycholic acid. R=—COOH; R'=—CH₂—CH₂—CONH₂)

The reaction of the triethylamine salt of glutamine with the ursodeoxycholic acid mixed anhydride occurs, as in the previous Examples, at a low temperature, without using a cooling bath and takes about 7 hours for completion. White crystals are obtained, chromatographically pure and melting at 110° C., with decomposition at 85°. The amount of free ursodeoxycholic acid is less than 0.5%, by quantitative alkalimetric analysis. The NMR and R spectra shown in FIGS. 7 and 8 confirm the structural formula.

EXAMPLE 5

Ca salt of taurinamide of ursodeoxycholic acid. (R=—CH₂—CH₂—SO₃H; R'=—H).

In this case too, the reaction of the mixed anhydride is carried out by slowly adding the organic amine salt of taurine at a low temperature. After 5 hours, with stirring, the formation of amide is completed, and the reaction mixture is acidified with HCl. The solution is then treated with CaC0₃ (no precipitation of a Ca salt is observed). The solution is concentrated to dryness, and taken up in chloroform to remove the organic amine hydrochloride. The chloroform phase is decanted and the oily, thick white substance is collected in acetone to complete crystallization. The resulting white crystals are chromatographically pure and have a melting point of 110° C. The amount of free ursodeoxycholic acid is less than 0.5% by quantitative alkalimetric analysis. The NMR and IR spectra shown in FIGS. 9 and 10 confirm the structural formula.

What is claimed is:

1. A compound of the formula:

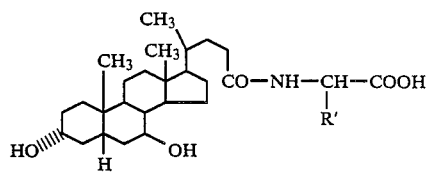

wherein R' is —(CH₂)₂—CONH₂, CH₂—CONH₂, —(CH₂)₂—SCH₃ or —CH₂—S—CH₂— COOH; or a salt of the compound with an organic or an inorganic pharmaceutically active base.

2. The salt according to claim 1, wherein the organic base is a basic aminoacid.

3. The salt according to claim 2, wherein the basic aminoacid is lysine or arginine.

4. The salt according to claim 1, wherein the inorganic base is sodium hydroxide or calcium hydroxide.

5. A compound or salt according to claim 1, 2, 3 or 4, wherein R' is —(CH₂)₂—CONH₂.

6. A compound or salt according to claim 1, 2, 3 or 4, wherein R' is —CH₂—CONH₂.

7. A compound or salt according to claim 1, 2, 3 or 4, wherein R' is —(CH₂)₂—SCH₃.

8. A compound or salt according to claim 1, 2, 3 or 4, wherein R' is —CH₂—S—CH₂—COOH.

9. A process for preparing a compound of the formula:

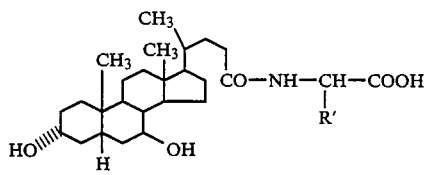

wherein R' is —(CH₂)₂—CONH₂, CH₂—CONH₂, —(CH₂)₂—SCH₃ or —CH₂—S—CH₂—COOH, which comprises reacting ursodeoxycholic acid with an alkyl chloroformate in the presence of an organic amine and in dioxane at a temperature of 0°–20° C. to form a mixed anhydride, adding an organic amine salt of methionine, carboxymethylcysteine, asparagine or glutamine to the cooled, mixed anhydride and allowing the amine salt and mixed anhydride to warm to room temperature.

10. A process according to claim 9, wherein the organic amine is triethylamine.

11. A process according to claim 9, wherein the alkyl chloroformate is ethyl, phenyl or isobutyl chloroformate.

* * * * *